(12) United States Patent
Hallen

(10) Patent No.: US 6,585,679 B1
(45) Date of Patent: Jul. 1, 2003

(54) SYSTEM AND METHOD FOR ENHANCING OXYGEN CONTENT OF INFUSION/ IRRIGATION FLUID FOR OPHTHALMIC SURGERY

(75) Inventor: Paul Hallen, Sparks, MD (US)

(73) Assignee: Retinalabs.Com, Atlanta, GA (US)

( * ) Notice: Subject to any disclaimer, the term of this patent is extended or adjusted under 35 U.S.C. 154(b) by 0 days.

(21) Appl. No.: 09/425,071

(22) Filed: Oct. 21, 1999

(51) Int. Cl.[7] .............................................. A61M 37/00
(52) U.S. Cl. ....................................................... 604/27
(58) Field of Search ............................. 604/26, 23, 24, 604/27

(56) References Cited

U.S. PATENT DOCUMENTS 3,628,532 A * 12/1971 Magrath
5,407,426 A *  4/1995 Spears
5,599,296 A *  2/1997 Spears
5,653,685 A *  8/1997 Klatz et al.
5,797,874 A *  8/1998 Spears
RE36,460 E  * 12/1999 Klatz et al.

OTHER PUBLICATIONS

Aaberg, Thomas. "Does Hyperoxygenation Limit Retinal Degeneration After Retinal Detachment?" American J. of Opthamology, Aug. 1999, 128(2)/231.

Lewis et al. "Limiting the Proliferation and Reactivity of Retinal Muller Cells During Experimental Retinal Detachment: The Value of Oxygen Supplementation" American J. of Opthamology, Aug. 1999; 128(2)/165–72.

* cited by examiner

Primary Examiner—Brian L. Casler
(74) Attorney, Agent, or Firm—Edwards & Angell, LLP; Peter F. Corless; Richard J. Roos

(57) ABSTRACT

A system and method are provided for oxygenating infusion/ irrigation fluid, and for providing the hyperoxic infusion/ irrigation fluid so formed to an ophthalmic surgical site.

11 Claims, 2 Drawing Sheets

SYSTEM AND METHOD FOR ENHANCING OXYGEN CONTENT OF INFUSION/ IRRIGATION FLUID FOR OPHTHALMIC SURGERY

BACKGROUND

1. Field of the Invention

The present invention generally relates to ophthalmic surgery. More particularly, the invention relates to systems for maximizing the oxygen content of infusion/irrigation fluids used in ophthalmic surgical procedures, and to methods for using the same.

2. Background

The use of infusion/irrigation fluids during the course of ophthalmic surgical procedures is well known. These fluids provide structural support and fluidic balance that keep the eye inflated during the manipulation and/or removal of tissue from within the eye.

It also is know in the art that invasive surgical procedures can negatively effect ocular tissue at the cellular level. For example, representative of the complications which can arise as a result of invasive ophthalmic surgical procedures are both the opacification of ocular tissues, and a reduction in the functionality and sensitivity of those tissues.

Further, it is well understood by those in the art that intraocular infusing/irrigating solutions can have adverse effects upon ocular morphology and function. Indeed, significant effort has been expended in the search for an optimal chemical composition for use as an intraocular infusion/ irrigating solution. More specifically, the goal of this effort has been (and is) to find a chemical composition that produces minimal negative effects upon the cellular structures of the eye, while at the same time, maximizing the patient's post-operative visual acuity. This effort has been successful to the extent in that some infusion fluids have been found to be less harmful to ocular anatomy and physiology than others. Nevertheless, a need still exists for an intraocular infusion/irrigation solution that will further minimize the negative effects of ophthalmic surgical stress.

SUMMARY OF THE INVENTION

The present invention provides an infusion/irrigation fluid administration system and method that maximizes the quantity of oxygen provided to the tissue of the eye during the course of ophthalmic surgical procedures.

In preferred embodiments, the invention includes a system that highly oxygenates the infusion/irrigation fluid used during the course of ophthalmic surgery substantially immediately prior to its introduction to the eye.

Addition of oxygen to infusion or irrigation fluid (i.e. infusion/irrigation fluid) can have a significantly positive effect to tissue affected by surgery, particularly in ophthalmic surgery. Accordingly, use of oxygenated fluids in accordance with the invention can positively impact potential surgical trauma particularly ophthalmic surgery, recovery from surgical procedures particularly ophthalmic surgery, and the like.

More particularly, in one preferred embodiment of the invention, an in-line, oxygenating chamber is provided in the infusion/irrigation fluid line between a fluid source and the infusion/irrigation site. Typically, the oxygenation chamber is located close to the operative site. This oxygenating chamber generally contains a gas permeable member (preferably diffusing member) that is supplied by an oxygen source. More specifically, the fluid flowing through the infusion/irrigation line is passed through the oxygenation chamber wherein oxygen travels through a gas permeable membrane or the like defining at least a portion of the diffusing gas permeable member, and diffuses into the fluid. This results in the provision of hyperoxic fluid directly to the ophthalmic surgical site.

In another preferred embodiment, an alternative oxygenating infusion/irrigation fluid administration system is provided. This system generally includes a fluid source; an I.V. administration spike; fluid tubing; atmospheric air vent tubing with a filter; a pressurized oxygen canister or lecture bottle; and appropriate adaptive connectors. In addition, the system may also optionally include a stopcock. In this embodiment, the oxygen is bubbled through the fluid in the source. Then the fluid is allowed to pass through the tubing to the operative site.

The invention can be employed with a wide variety of surgical procedures for delivery of fluid to a surgical site. However, the invention is particularly useful for delivery of oxygenated fluid to an opththalmic surgical site (e.g. to or proximate to a patient's eye), such as by infusing the oxygenated fluid into a patient's eye.

BRIEF DESCRIPTION OF THE DRAWINGS

These, and other features and advantages of the invention, will become clear to those skilled in the art from the following detailed description of the preferred embodiments of the invention rendered in conjunction with the appended drawings in which like reference numerals refer to like elements throughout, and in which.

DETAILED DESCRIPTION OF THE INVENTION

Figure 1:
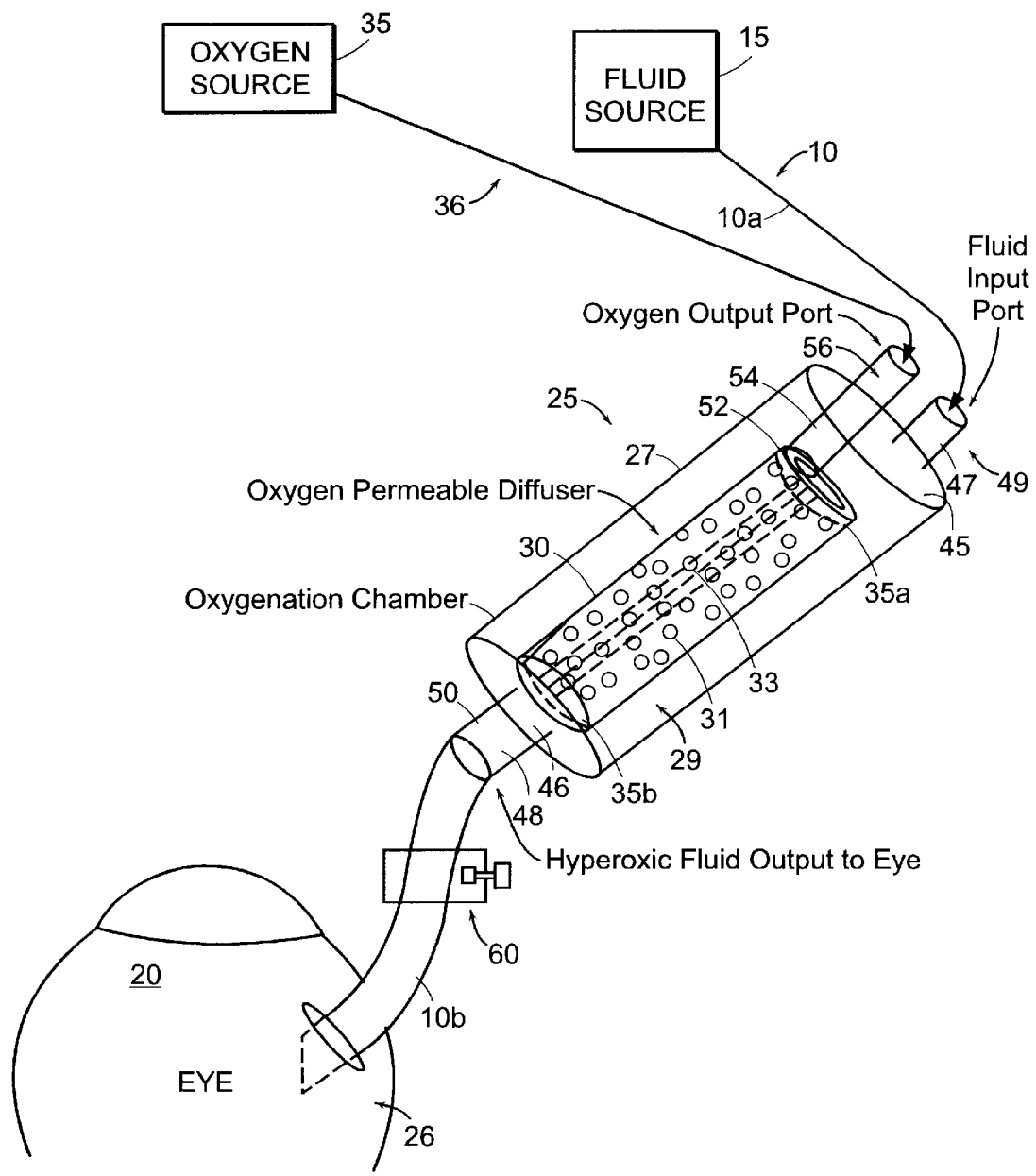
FIG. 1 is an illustrative, diagrammatic view showing an oxygenation unit located in an infusion/irrigation fluid line close to the eye, and sources of infusion/irrigation fluid and oxygen associated therewith; and, FIG. 2 is an illustrative, diagrammatic view of another infusion/irrigation fluid oxygenation system in accordance with the present invention.

Referring now to the drawings, and particularly to FIG. 1, there is shown an illustrative, diagrammatic view of one preferred embodiment of the invention. In this embodiment, a fluid tube, generally indicated at 10, extends from a fluid source 15 to the eye 20 of the patient. An in line, oxygenating chamber, generally indicated at 25, is provided in the fluid line 10 close to the ophthalmic surgical site, generally indicated at 26.

The oxygenating chamber 25 includes a substantially totally enclosed, hollow, outer body 27 containing a diffusing gas permeable member 30. The interior of body 27 is supplied with infusion/irrigation fluid through line 10a, and diffusing gas permeable member 30 is supplied by a pressurized oxygen source 35 through tubing, generally indicated at 36. The interior of body 27 also is connected to the ophthalmic surgical site by tubing, generally indicated at 10b.

More specifically, the oxygenating chamber 25 includes outer body 27 defining an internal volume 29, and end ports 45 and 46 connected to the lumens 47 and 48 of input and output connectors 49 and 50, respectively. In the particular embodiment shown, connectors 49 and 50 extend outwardly from opposite ends of cylindrical, outer, hollow body 27. Outer body 27, for example, may be approximately four (4)

inches long and approximately 0.75 inches in diameter. It is to be understood, however, that other shapes and dimensions are contemplated to be within the scope of this invention in its broadest aspects.

Diffusing gas permeable member 30 may be substantially cylindrical, and is formed (at least in part) of a gas permeable membrane or other gas permeable material. In the embodiment shown in the drawing, diffusing gas permeable member 30 is a hollow, cylindrical element slightly shorter than body 27, and encloses an internal substantially cylindrical volume 31. Again, it is to be understood that the dimensions and shape of the diffusing gas permeable member 30 may be other than cylindrical without departure from the present invention in its broadest aspects. Indeed, since a goal of the invention is to highly oxygenate the infusion/irrigation fluid, the greater the area of contact between the gas permeable portion of member 30 and the interior volume 29 of chamber 25 is, the better the diffusion of oxygen into the fluid will become. Accordingly, not only does the shape of member 30 not have to be cylindrical, but also, as shown in phantom at 33 in FIG. 1, member 30 may be made up of a plurality of hollow elements 31 extending in the direction of fluid flow between manifolds 35a and 35b. A port 52 at one end of the member 30 connects the internal volume 31 of the member 30 to the lumen 54 of a connection member 56 that extends from the member 30 through an end of the body 27.

A gas transfer tube 36 connects pressurized oxygen source 35 to connector 56 such that oxygen under pressure may be provided to the interior of volume 31 of member 30. In addition, a stopcock 60 may be provided around line 10b for limiting the flow of infusion/irrigation fluid to the ophthalmic surgical site 26.

All of the above referred to connections are fluid tight to prevent gas and/or infusion/irrigation fluid leakage. For example, the gas transfer tubing 36 might fit tightly over a connector 56 provided with an enlarged outer end (not shown). In such a case, the tubing 36 may be held in place by a screw or spring clamp (not shown) engaging the outer surface of the tubing between the end of body 27 and the enlarged end of connector 56. Similarly, the outer ends of fluid connectors 49 and 50 may be sized to tightly exteriorly receive ends of infusion tubing 10. Further, the material of the connectors may be chosen such that spring or screw clamps may be utilized without breakage thereof and/or the connectors may be crimped against the end of an infusion/irrigation fluid tube inserted therein.

In this way, a system is provided wherein infusion/irrigation fluid flowing through an infusion line to an ophthalmic surgical site is passed through an in line oxygenation chamber. As the infusion fluid flows through the chamber, oxygen passes through a gas permeable portion of an element located internally of the chamber, and diffuses into the fluid. This results in the desired provision of hyperoxic infusion irrigation fluid directly the ophthalmic surgical site.

As discussed above, preferably the fluid is oxygenated substantially immediately prior to delivery of the oxygenated fluid to an ophthalmic surgical site, such as delivery to a patient's eye or proximate thereto where surgery is being performed. "Oxygenation substantially immediately prior to delivery of the fluid" is recognized herein as indicating that the fluid has been oxygenated at least the same day (within 24 hours) as fluid application, more typically within about 6, 5, 4, 3, 2, 1, 0.5 or 0.25 hours prior to fluid delivery to a surgical site. Particularly preferred is where the fluid is delivered to a surgical site within about 5, 4, 3, 2, 1, or about 0.5 minutes after oxygenation treatment. A preferred system is where the oxygenation is performed in the fluid flow path from the fluid source to the delivery surgical site. The in-line oxygenation system depicted in the figures exemplifies such flow-path oxygenation.

Further, oxygenation treatment of a fluid in accordance with the present invention preferably increases the oxygen content of the fluid by at least about 0.5, 1, 2 or 3 molar percent, relative to the oxygen content of the fluid without the oxygenation treatment, and more preferably the oxygen content of the fluid is increased by at least about 4, 5, 6, 7, 8, 9, or 10 mole percent, relative to the oxygen content of the fluid without the oxygenation treatment.

Additionally, references herein to oxygenating a fluid indicate that the fluid is exposed to oxygen, which exposure can be by performed by a wide variety of methods. While the bubbling oxygen through a fluid particularly as exemplified herein is a generally preferred oxygenation treatment, other procedures also may be suitably employed.

Figure 2:
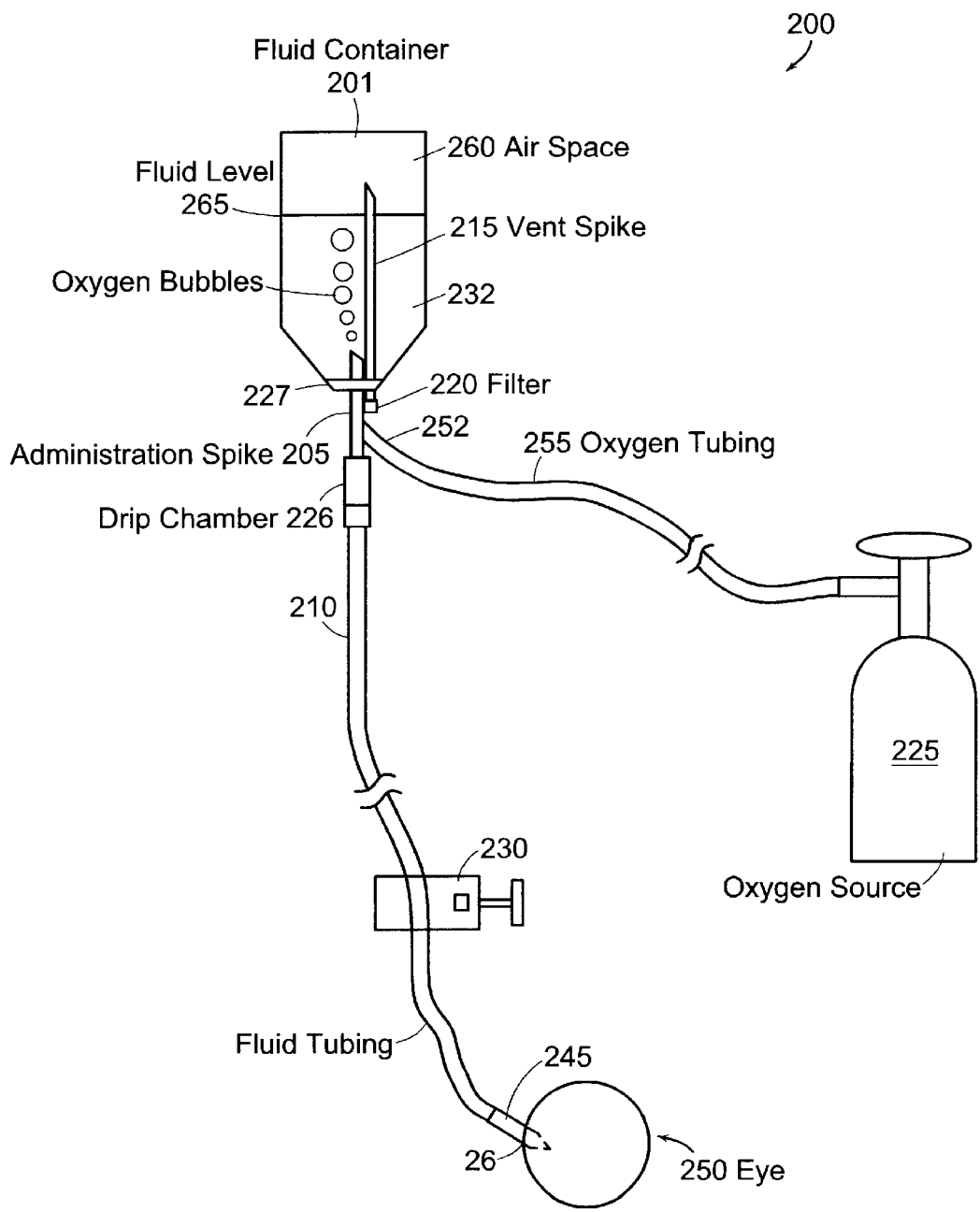

In an alternative embodiment of the invention, illustratively depicted in FIG. 2, the system is generally indicated at 200. The system generally includes (i) an infusion/irrigation fluid container 201; (ii) an I.V. administration spike 205; (iii) fluid infusion tubing 210; (iv) atmospheric air vent spike/tubing 215 with a filter 220; (v) a pressurized oxygen canister or lecture bottle 225; and (vi) appropriate adaptive connectors, such as drip chamber 226, and fluid container closure member 227. In addition, the system also may optionally include a stopcock 230.

The administration spike 205 is adapted to penetrate the fluid container closure member 227 thereby providing an interface to the fluid in container 201. In this embodiment, the infusion/irrigation fluid 232 is supplied to the ophthalmic surgical site 26 by gravity feed. Hence, it will be understood that the infusion fluid travels from the container 201 through the spike 205, through the infusion tubing 210, past optional stopcock 230, to a cannula 245 that interfaces with the eye 250. Further, administration spike 205 also includes a side connector 252 that provides an input path from the oxygen source 225 through gas line 255 to the interior of fluid container 201.

The operation of the system depicted in FIG. 2 now will be discussed.

Oxygen is allowed to enter the administration spike 205 through connector 252 and tubing 255, which is interfaced with the pressurized oxygen source 225. In this regard, it should be understood that the oxygen might either travel through a separate internal lumen (not shown) within spike 205 into container 201, or alternatively, travel upward through the same lumen through which the infusion/irrigation fluid flows downwardly toward the eye 250. Stated slightly differently, the pressure within the airspace 260 above the fluid level 265 in the container 201 can be controlled in combination with the cross-sectional area of the infusion tubing and the volume of oxygen introduced through the interface over time. Thus, in appropriate circumstances, liquid may be allowed to flow downwardly through the tube, while, at the same time, oxygen bubbles are allowed to flow upwardly through the spike 205. Oxygen, therefore, is caused continuously bubble up through the infusion fluid in the container 201. As the oxygen bubbles flow upwardly through the fluid, oxygen diffuses into the fluid.

The vent spike 215 also penetrates the container closure 227. However, instead of remaining close to the inner side of the closure member as the end of the administration spike 205 does, the vent spike projects into air space 260 above the fluid in container 201. The vent spike typically includes an external filter 220 to maintain the purity of the infusion fluid. As will be seen from the drawings, the venting structure provides a continuous open passageway from air space 260 to the outside atmosphere. Accordingly, excess oxygen not diffused into the infusion/irrigation fluid does not adversely increase the pressure in the container. The result is that the oxygen content of the infusion/irrigation fluid provided to the eye is maximized (i.e., hyperoxic fluid is provided to the eye during ophthalmic surgery in a manner that provides maximum protection for the ocular tissues with which it comes in contact). The maximum post-operative visual acuity result possible as it relates to the characteristics of the infusion fluid utilized are thereby achieved.

It is to be understood that the foregoing specification has been presented by way of illustration only, and not limitation. Numerous alterations, changes, modifications, variations and the like will occur to those skilled in the art in view of the above described preferred embodiments of the present invention. Accordingly, the present invention is to be understood as being limited only by the terms of the claims appended hereto.

What is claimed is:

1. A method for oxygenating fluid for delivery to an ophthalmic surgical site, comprising:

providing a system for oxygenating fluid during the course of ophthalmic surgical procedures; and oxygenating fluid for delivery, via delivery and gas permeable apparatus, to an ophathalmic surgical site substantially immediately prior to the delivery of the oxygenated fluid to the ophthalmic surgical site, wherein both the delivery apparatus and the gas permeable apparatus are adapted to have an orientation with respect to the ophthalmic surgical site that enables delivery of the oxygenated fluid to the ophthalmic surgical site in a substantially constant direction.

2. The method of claim 1 wherein the fluid is oxygenated by gas diffusion.

3. The method of claim 1 wherein the surgical site is infused or irrigated with the oxygenated fluid.

4. The method of claim 1 wherein the fluid is oxygenated in a housing positioned in the flow path of the fluid from the fluid source to the surgical site.

5. The method of claim 1 wherein the fluid is oxygenated in a housing.

6. The method of claim 1 wherein the system comprises a cylindrical housing for oxygenating the fluid.

7. A method for oxygenating infusion/irrigation fluid for delivery to a surgical site, comprising:

(a) providing a system for oxygenating infusion/irrigation fluid during the course of ophthalmic surgical procedures comprising:

a source of oxygen gas;

a source of infusion/irrigation fluid;

delivery apparatus for the controlled delivery of infusion/irrigation fluid from said infusion/irrigation fluid source to an ophthalmic surgical site; and gas permeable apparatus connected to the source of oxygen gas and to the delivery apparatus; and (b) oxygenating said infusion/irrigation fluid immediately prior to the delivery of the infusion/irrigation fluid to the ophthalmic surgical site, wherein both the delivery apparatus and the gas permeable apparatus are adapted to have an orientation with respect to the ophthalmic surgical site that enables delivery of the oxygenated fluid to the ophthalmic surgical site in a substantially constant direction.

8. A method of claim 7 wherein the housing comprises an oxygen permeable material.

9. A method for oxygenating fluid for delivery to an ophthalmic surgical site, comprising:

providing a system for oxygenating fluid during the course of ophthalmic surgical procedures;

oxygenating fluid for delivery to an ophthalmic surgical site substantially immediately prior to the delivery of the fluid to the ophthalmic surgical site; and delivering the oxygenated fluid to the ophthalmic surgical site substantially immediately after oxygenating and in a substantially constant direction.

10. The method of claim 9 wherein the fluid is delivered to the surgical site within about 30 seconds after oxygenation.

11. The method of claim 9 wherein oxygenation is performed in the fluid flow path from the fluid source to the surgical site.

* * * * *